(12) United States Patent
Bourassa et al.

(10) Patent No.: US 6,846,930 B2
(45) Date of Patent: Jan. 25, 2005

(54) HETEROCYCLO-ALKYLSULFONYL PYRAZOLE DERIVATIVES

(75) Inventors: Dennis E. Bourassa, Norwich, CT (US); Michael J. Castaldi, Pawcatuck, CT (US); David B. Ripin, Old Saybrook, CT (US)

(73) Assignee: Pfizer Inc., Kalamazoo, MI (US)

( * ) Notice: Subject to any disclaimer, the term of this patent is extended or adjusted under 35 U.S.C. 154(b) by 72 days.

(21) Appl. No.: 10/648,588

(22) Filed: Aug. 25, 2003

(65) Prior Publication Data

US 2004/0044042 A1 Mar. 4, 2004

Related U.S. Application Data

(62) Division of application No. 10/256,432, filed on Sep. 27, 2002, now Pat. No. 6,646,128.
(60) Provisional application No. 60/325,647, filed on Sep. 28, 2001.

(51) Int. Cl.[7] .............................................. C07D 401/04
(52) U.S. Cl. ................. 546/268.4; 546/275.4
(58) Field of Search ............................ 546/268.4, 275.4

(56) References Cited

U.S. PATENT DOCUMENTS

| | | | |
|---|---|---|---|
| 6,506,779 B1 | 1/2003 | Cheng et al. | ................ 514/341 |
| 6,531,492 B1 | 3/2003 | Lundy et al. | ................ 514/341 |

FOREIGN PATENT DOCUMENTS

| | | | | |
|---|---|---|---|---|
| EP | 0418845 | 9/1990 | ......... | C07D/231/14 |
| EP | 0554829 | 2/1993 | ......... | C07D/231/12 |
| EP | 1104758 | 11/2000 | ......... | C07D/401/04 |
| EP | 1104759 | 11/2000 | ......... | C07D/405/14 |
| WO | WO9500501 | 1/1995 | ......... | C07D/277/02 |
| WO | WO9515315 | 6/1995 | ......... | C07D/231/12 |
| WO | WO9515316 | 6/1995 | ......... | C07D/231/12 |
| WO | WO9515317 | 6/1995 | ......... | C07D/231/12 |
| WO | WO9515318 | 6/1995 | ......... | C07D/231/12 |
| WO | WO9603387 | 2/1996 | ......... | C07D/233/54 |
| WO | WO9603392 | 2/1996 | ......... | C07D/277/26 |
| WO | WO9608482 | 3/1996 | ......... | C07D/307/58 |
| WO | WO9619469 | 6/1996 | ......... | C07D/307/58 |
| WO | WO9636623 | 11/1996 | ......... | C07D/307/60 |
| WO | WO9711704 | 4/1997 | ......... | A61K/31/635 |
| WO | WO9713755 | 4/1997 | ......... | C07D/231/12 |
| WO | WO9714691 | 4/1997 | ......... | C07D/307/58 |
| WO | WO9716435 | 5/1997 | ......... | C07D/307/32 |
| WO | WO 01/40216 A1 * | 6/2001 | ......... | C07D/401/04 |
| WO | WO0140216 | 6/2001 | ......... | C07D/401/04 |

OTHER PUBLICATIONS

Avis, "Parenteral Preparations", *Remington's Pharmaceutical Sciences* 18[th] Ed., Gennaro ed., pp. 1545–1580 (1990).
*Hawley's Condensed Chemical Dictionary*, 13[th] ed. John Wiley & Sons, NY, p. 1034 (1997).
*Aust. J. Chem.* 30, p. 229 (1977).
Ohta, et al., "Palladium–catalyzed Arylation of Furan, Thiophene, Benzo[b]thiophene", *Heterocycles* 31(11), pp. 1951–1958 (1990).
Zelenin, et al., "5–Hydroxy–4,5–Dihydropyrazoles", *Tetrahedron* 51(41), pp. 11251–11256 (1995), xp002222133.
Database Crossfire Beilstein 'Online? Reaction ID 740522, XP002222134, abstract 1958.
Finar, et al., "The Reaction between Aroylacctones and Arylhydrazines", *J.Chem. Soc.*, pp. 200–203 (1958).
Database Crossfire Beilstein 'Online?, Reaction ID 2986667, XP002222135, abstract 1991.
Black, et al., "Synthesis of 7–Substituted Indoles as Potential Ligand Precursors", *Aust. J. Chem.* 44, pp. 1771–1781 (1991).
Database Crossfire Beilstein 'Online?, Reaction ID 3460702, XP002222136, abstract 1989.
Fatutta, et al., Synthesis of Tetrahydorthipyrano[3,2–c]pyrazole Derivatives from 3–Thianones, *J. Heterocyclic Chem.* 26, pp. 183–187 (1989).
Database Crossfire Beilstein 'Online?, Reaction ID 3395297, XP–002222137, abstract 1989.
Ahluwalia, et al., "Synthesis and antimicrobial activities of some new 1–substituted–3–92'hydrosyaryl)–5–phenylpyrazoles and 1–substituted–5aryl–3–methyl–4–(N[1]–substituted p–sulphamylbenzeneazo)pyrazoles", *Indina Journal of Chemistry* 28B, pp. 150–153 (1989).
Database Crossfire Beilstein 'Online?, Reaction ID 354358, XP–002222138, abstract 1958.
Fattuta, et al., "On the ethyl ester of p–phenyl–benzoylpyruvic acid and some of its cyclization products" *Gazz. Chim. Ital.* 88, pp. 899–909 (1958).

* cited by examiner

*Primary Examiner*—Mark Kopec
*Assistant Examiner*—Eisa Elhilo
(74) *Attorney, Agent, or Firm*—Martha Munchhof

(57) ABSTRACT

The invention relates to compounds of formula 4:

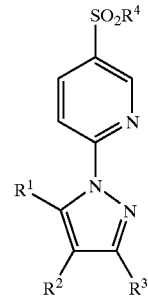

Wherein R1–R4 are defined as in the specification.

1 Claim, No Drawings

HETEROCYCLO-ALKYLSULFONYL PYRAZOLE DERIVATIVES

CROSS-REFERENCE TO RELATED APPLICATION

This application is a division of U.S. Ser. No. 10/256,432, filed on Sep. 27, 2002, now U.S. Pat No. 6,646,128, which claims the benefit of U.S. Provisional Patent Application No. 60/325,647, filed on Sep. 28, 2001.

BACKGROUND OF THE INVENTION

This invention relates to processes for the regioselective preparation of heterocyclo-alkylsulfonyl pyrazole derivatives and their synthetic intermediates. The pyrazole compounds prepared by the processes of this invention are useful in the treatment or alleviation of inflammation and other inflammation associated disorders, such as arthritis, neurodegeneration and colon cancer, in mammals, preferably humans, dogs, cats or livestock. It is believed that the pyrazole compounds prepared by the processes of this invention inhibit the biosynthesis of prostaglandins by intervention of the action of the enzyme cyclooxygenase on arachidonic acid.

Nonsteroidal anti-inflammatory drugs (NSAIDs) are widely used in treating pain and the signs and symptoms of arthritis because of their analgesic and anti-inflammatory activity. It is accepted that common NSAIDs work by blocking the activity of cyclooxygenase (hereinafter referred to as "COX"), also known as prostaglandin G/H synthase (PGHS), the enzyme that converts arachidonic acid into prostanoids. Prostaglandins, especially prostaglandin $E_2$ ($PGE_2$), which is the predominant eicosanoid detected in inflammation conditions, are mediators of pain, fever and other symptoms associated with inflammation. Inhibition of the biosynthesis of prostaglandins has been a therapeutic target of anti-inflammatory drug discovery.

A variety of sulfonylbenzene compounds which inhibit COX have been disclosed in patent publications (WO 97/16435, WO 97/14691, WO 96/19469, WO 96/36623, WO 96/03392, WO 96/03387, WO 97/727181, WO 96/936617, WO 96/19469, WO 96/08482, WO 95/00501, WO 95/15315, WO 95/15316, WO 95/15317, WO 95/15318, WO 97/13755, EP 0799523, EP 418845, and EP 554829). International Publication Number WO 97/11704 discloses pyrazole compounds substituted by optionally substituted aryl.

The production of the compounds of formula 1 with a yield and purity suitable for commercial use has presented several difficulties. As described in detail below, the use of previously disclosed methods results in the production of significant amounts of the regioisomer of the compound of formula 1, which is difficult to separate from the compound of formula 1 without significant loss of yield. Applicants' investigations have revealed that preparing the compound of formula 1 at low temperatures favors the regioselective production of the compound of formula 1 but provides poor yields and the presence of an intermediate as a major impurity. On the other hand, maintaining the reaction temperature high enough to allow the consumption of the intermediates causes another problem, namely, the production of the regioisomer of the compound of formula 1.

Applicants solved these problems by discovering unexpectedly that the use of water as a co-solvent in the reaction provided the following benefits: (1) the production of the regioisomer of the compound of formula 1 is minimized, thereby resulting in the formation of the compound of formula 1 with high regioselectivity; and (2) the compound of formula 1 is formed with high yield. In addition, the use of water allows the regioselective production of the compound of formula 1 over a broad range of temperatures.

SUMMARY OF THE INVENTION

The present invention relates to a process for preparing a compound of formula 1:

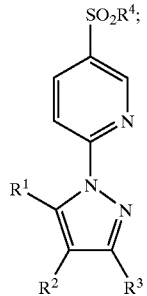

which comprises combining
(a) a compound of formula 2:

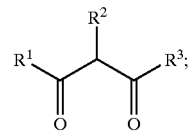

(b) a compound of formula 3:

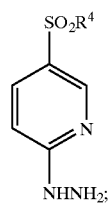

(c) one or more acids;
(d) one or more water-miscible organic solvents; and
(e) water;
wherein
$R^1$ is phenyl optionally substituted by 1–3 substituents independently selected from the group consisting of halo, hydroxy, cyano, mercapto, $(C_1-C_6)$alkyl, $(C_2-C_6)$alkenyl, $(C_1-C_6)$alkoxy, —$OCF_3$, $(C_1-C_6)$alkyl-S—, $(C_1-C_6)$alkyl-S(=O)—, $(C_1-C_6)$alkyl-$SO_2$—, amino, $(C_1-C_6)$alkylamino, di[$(C_1-C_6)$alkyl]amino, $H_2N$—(C=O)—, $(C_1-C_6)$alkyl-NH—(C=O)— and formyl;
$R^2$ is hydrogen, halo or $(C_1-C_6)$alkyl;
$R^3$ is $(C_1-C_6)$alkyl optionally substituted with from one to three halo atoms; and
$R^4$ is $(C_1-C_6)$alkyl.

In an embodiment of the invention, $R^1$ is phenyl optionally substituted with one or two substituents independently selected from halo, hydroxy, mercapto, $(C_1-C_6)$alkyl, $(C_1-C_6)$alkoxy and $(C_1-C_6)$alkyl-S—. In a preferred embodiment of the invention, $R^1$ is unsubstituted phenyl.

In another embodiment of the invention, $R^2$ is chloro or fluoro. In a preferred embodiment of the invention, $R^2$ is chloro. In another preferred embodiment of the invention, $R^2$ is $(C_1-C_6)$alkyl; in a more preferred embodiment of the invention, $R^2$ is hydrogen or methyl. In a particularly preferred embodiment of the invention, $R^2$ is hydrogen.

In another embodiment of the invention, $R^3$ is $(C_1-C_6)$ alkyl substituted with from one to three halo atoms. In a preferred embodiment of the invention, $R^3$ is $(C_1-C_3)$alkyl substituted with from one to three fluoro atoms. In a more preferred embodiment of the invention, $R^3$ is difluoromethyl or trifluoromethyl. In a particularly preferred embodiment of the invention, $R^3$ is difluoromethyl. In another particularly preferred embodiment of the invention, $R^3$ is trifluoromethyl.

In another preferred embodiment of the invention, $R^4$ is $(C_1-C_3)$alkyl. In a more preferred embodiment of the invention, $R^4$ is methyl.

In another embodiment of the invention, $R^1$ is unsubstituted phenyl and $R^2$ is hydrogen. In another embodiment of the invention, $R^1$ is unsubstituted phenyl, $R^2$ is hydrogen, $R^3$ is methyl substituted with one, two or three fluoro and $R^4$ is methyl. In a preferred embodiment of the invention, $R^1$ is unsubstituted phenyl, $R^2$ is hydrogen, $R^3$ is difluoromethyl or trifluoromethyl and $R^4$ is methyl. In a particularly preferred embodiment of the invention, $R^1$ is unsubstituted phenyl, $R^2$ is hydrogen, $R^3$ is difluoromethyl and $R^4$ is methyl.

In this application, the term "compound of formula 1" includes a compound of formula 1 as well as a compound of formula 1a, wherein $R^3$ is trifluoromethyl or difluoromethyl, and a compound of formula 1b:

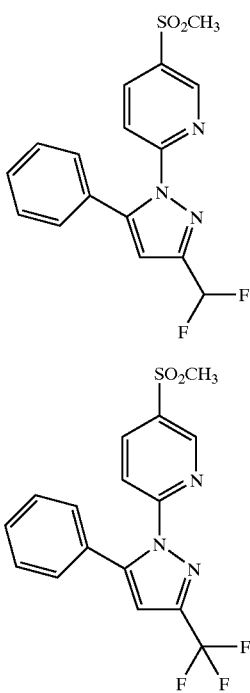

The compounds of formula 1a and formula 1b are preferred embodiments of the compound of formula 1, to which all of the embodiments, preferred embodiments and particularly preferred embodiments of the processes described herein apply. The compound of formula 1a is a particularly preferred embodiment of the compound of formula 1, to which all of the embodiments, preferred embodiments and particularly preferred embodiments of the processes described herein apply. Accordingly, for the sake of brevity, the phrase "process for preparing a compound of formula 1" is to be understood for the purposes of this application as interchangeable with the phrase "process for preparing the compound of formula 1a" or the phrase, "process for preparing the compound of formula 1b." It is to be further understood that the compounds of formula 2 and formula 3 used in the processes of the invention for preparing the compounds of formula 1a and formula 1b are to be understood as including the corresponding respective preferred substituents. For example, in a process for preparing a compound of formula 1a, in the compound of formula 2, $R^1$ is unsubstituted phenyl, $R^2$ is hydrogen and $R^3$ is difluoromethyl, while in the compound of formula 3, $R^4$ is methyl. Correspondingly, in a process for preparing the compound of formula 1b, in the compound of formula 2, $R^1$ is unsubstituted phenyl, $R^2$ is hydrogen and $R^3$ is trifluoromethyl, while in the compound of formula 3, $R^4$ is methyl.

It is to be noted that the term "mixture", as used herein, unless otherwise indicated, is used without regard to the state of dispersion of the components thereof.

The term "miscible" as used herein with respect to two or more substances, unless otherwise indicated, means that the two or more substances are capable of forming a "true solution" as that term is understood in the art (see, e.g., *Hawley's Condensed Chemical Dictionary*, 13th ed. John Wiley & Sons, New York (1997), p. 1034).

For example, the term "water-miscible" as used herein with respect to a particular component of a mixture containing at least water, means that the component is capable of forming a true solution with water. It is to be understood that any particular substance, viewed as a solute, may be capable of forming a true solution with a particular solvent only over a limited range of relative proportions or concentrations, i.e., the miscibility of any particular solute is typically limited according to (to name but a few examples of well-known relevant factors): the temperature of the mixture, the ambient pressure, the chemical properties of the solute and solvent, as well as the presence of other solutes and/or solvents whose chemical properties and relative proportions may affect the miscibility of the solute of interest.

The phrase "organic solvent" as used herein, unless otherwise indicated, means a non-aqueous solvent or mixture of non-aqueous solvents.

In an embodiment of the invention, the one or more water-miscible organic solvents comprise one or more water-miscible alcohols. In a preferred embodiment of the invention, the one or more water-miscible alcohols contain from 1 to 12 carbon atoms. In a more preferred embodiment of the invention, the one or more water-miscible alcohols are selected from the group consisting of methanol, ethanol, n-propanol, isopropanol, n-butanol, sec-butanol and tert-butanol. In a particularly preferred embodiment of the invention, the water-miscible alcohol is ethanol or isopropanol. In another particularly preferred embodiment of the invention, the water-miscible alcohol is isopropanol.

In another embodiment of the invention, the one or more acids are selected from the group consisting of hydrochloric acid, acetic acid, trifluoroacetic acid, p-toluenesulfonic acid and sulfuric acid. In a preferred embodiment of the invention, the acid is sulfuric acid.

In another embodiment of the invention, (a) and (b) are combined in the presence of (e). In a preferred embodiment of the invention, (a) is combined with a mixture of at least (b) and (e). In another preferred embodiment of the invention, (a) is combined with a mixture of at least (b), (c) and (e), and in a more preferred embodiment of the invention, the mixture of (b), (c) and (e) is prepared by combining (b) with a mixture of at least (c) and (e).

In another embodiment of the invention, a mixture of at least (a) and (d) is combined with the mixture of at least (b) and (e), and in a preferred embodiment of the invention, a mixture of (a) and (d) is combined with a mixture of (b), (c) and (e).

In another embodiment of the invention, (a) and (b) are combined before the addition of (e). In another embodiment of the invention, (a), (b) and (d) are combined before the addition of (e). In still another embodiment of the invention, (a), (b) and (c) are combined before the addition of (e), and in a preferred embodiment of the invention, (a), (b), (c) and (d) are combined before the addition of (e).

In another embodiment of the invention, the temperature is maintained at a temperature lower than the reflux temperature of the combination of (a), (b), (c) and (d). In another embodiment of the invention the temperature is maintained at a temperature lower than the reflux temperature of the combination of (a), (b), (c), (d) and (e).

In any embodiment of the invention wherein (a) and (b) are combined, the process of preparing a compound of formula 1 further comprises, after (a) and (b) are combined, maintaining the temperature below about 40° C. until the amount of (b) has decreased to less than about 10% of its initial value. In a preferred embodiment of the invention, the process for preparing a compound of formula 1 further comprises, after (b) has decreased to less than about 10% of its initial value, increasing the temperature to at least about 30° C.

In another embodiment of the invention, the process of preparing a compound of formula 1 further comprises maximizing the conversion to the compound of formula 1 of an intermediate of the formula 4:

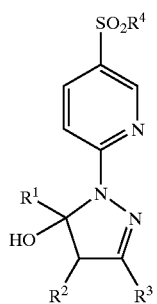

4 referred to herein as the "5-hydroxy precursor to the compound of formula 1", wherein $R^1$–$R^4$ are as defined hereinabove for the compound of formula 1, including the embodiments, preferred embodiments, more preferred embodiments and particularly preferred embodiments of the compound of formula 1. This invention further relates to a compound of formula 4. In an embodiment, the compound of formula 4 is in a substantially pure form. In a preferred embodiment, the compound of formula 4 is 90% pure.

In another embodiment of the invention, the process of preparing a compound formula 1 further comprises maintaining the temperature of at least about 30° C. until the molar amount of the 5-hydroxy derivative of the compound of formula 1 is less than about 10% of the initial molar amount of (b).

In an embodiment of the invention, the process of preparing a compound of formula 1 further comprises, after (a) and (b) are combined and after the amount of (b) has decreased to less than about 10% of its initial value, adding (e). In a preferred embodiment of the invention, (e) is added after the amount of (b) is less than about 5% of its initial value.

In an embodiment of the invention, the process of preparing a compound of formula 1 further comprises removing the acid from the combination of (a), (b), (c), (d) and (e) after the formation of the compound of formula 1 is substantially complete. In an embodiment of the invention, the acid is removed by washing a solid sample of the compound of formula 1. In another embodiment of the invention, the acid is removed by neutralization with a base. In this application, the phrase "substantially complete", unless otherwise specified, means that the molar amount of the referenced compound is at least about 90% of the molar amount of the limiting reagent used in its preparation. For example, in the above embodiment of the process of the invention, the formation of the compound of formula 1 is substantially complete when the molar amount of the compound of formula 1 is at least about 90% of the lesser of the molar amount of (a) the compound of formula 2 or (b) the compound of formula 3. It is to be understood that the percentage yield of a referenced compound is generally lower than the percentage of completion of the reaction, due to processing and purification losses, e.g. upon washing and/or recrystallization of the compound of formula 1.

In an embodiment of the invention, the processes of the invention produce a compound of formula 1 which is at least 90% pure, preferably at least 95% pure, more preferably at least 97% pure, and most preferably, at least 99% pure. It is to be understood that any compound which is produced in a process of the invention, other than the compound of formula 1, is to be considered an impurity, the amount of which is to be compared to the total yield of the process in order to calculate the percent purity of the compound of formula 1. Accordingly, a compound of formula 1 which is "90% pure" means a substance containing 90% by mass of the compound of formula 1, and 10% by mass in total of all other compounds, including any residual solvent(s) (including water) used in the process of the invention which are not removable by conventional drying techniques such as those described herein, e.g., blow drying, vacuum drying in an oven, e.g., at a temperature up to about 50° C.

In an embodiment of the invention, the process for preparing a compound of formula 1 further comprises granulating the combination of (a), (b), (c), (d) and (e). In a preferred embodiment of the invention, the combination is granulated for at least about 2 hours.

In a particularly preferred embodiment of the invention, $R^1$ is unsubstituted phenyl and $R^2$ is hydrogen.

In another particularly preferred embodiment of the invention, $R^3$ is difluoromethyl or trifluoromethyl.

In another particularly preferred embodiment of the invention, $R^4$ is methyl.

In another particularly preferred embodiment of the invention, $R^3$ is difluoromethyl.

In an embodiment of the invention, the molar amount of the compound of formula 2 is about the same as the molar amount of the compound of formula 3.

Examples 1–4 each set forth preferred embodiments of the invention, of which Example 3 is a preferred embodiment, and of which Example 4 is a particularly preferred embodiment.

In an embodiment of the invention, the processes of the invention produce an amount of a compound of formula 6 which is less than 10% of the amount of the compound of formula 1, preferably, less than 5%, and more preferably, less than 2%. In a particularly preferred embodiment of the invention, the processes of the invention produce an amount of a compound of formula 6 which is less than 1% of the amount of the compound of formula 1. It is to be understood that in this invention, the relative amounts of any two compounds, for example, the compounds of formula 1 and formula 6, may be determined by any means available to the ordinary practitioner, e.g., chromatographic, spectrometric and spectroscopic methods, and that the method is to be chosen according to the desired level of sensitivity, e.g., 10%, 5%, 2%, 1% of one particular component relative to another. In an embodiment, the relative amounts of the compounds of formula 1 and formula 6 are determined by chromatography, preferably, HPLC (high performance liquid chromatography) or TLC (thin-layer chromatography). In a particularly preferred embodiment, the relative amounts of the compounds of formula 1 and formula 6 are determined by HPLC. In another embodiment, the relative amounts of the compounds of formula 1 and formula 6 are determined by spectroscopic methods, preferably, IR (infrared) or NMR (nuclear magnetic resonance) spectroscopy.

Impurities which are currently known to result from carrying out the process of this invention, wherein the product of the reaction is the compound of formula 1a, include in addition to starting material impurities (i.e., in the compounds of formulas 2 and 3), residual intermediates (i.e., the compounds of formulas 4 and 5) and the compound of formula 6, are the following compounds:

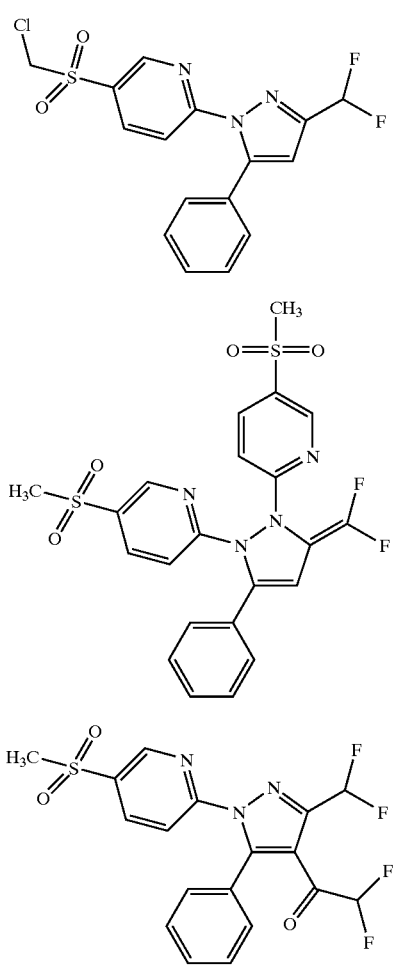

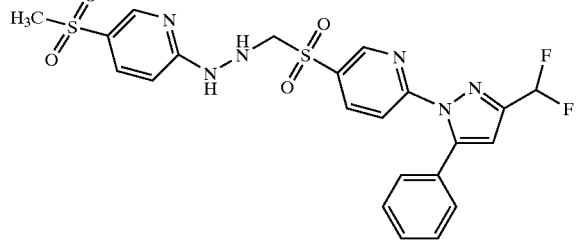

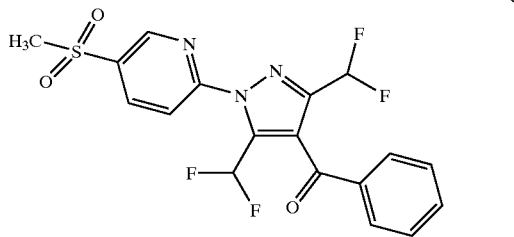

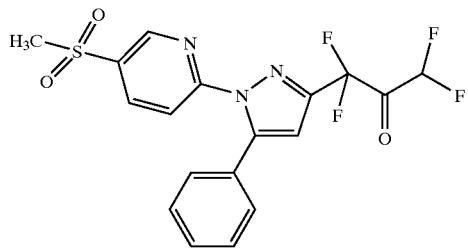

In addition, in a process for preparing a compound of formula 1a, i.e., wherein $R^3$ is difluoromethyl, the compound wherein $R^3$ is trifluoromethyl (i.e., a compound of formula 1b) has sometimes also been detected as an impurity.

In an embodiment of the processes described herein, the reaction is carried out at about atmospheric pressure. In this application, the term "atmospheric pressure" means a pressure within the normal range of meteorologic atmospheric pressure for a particular altitude, while the term "elevated pressure" means a pressure above atmospheric pressure. In another embodiment of the processes described herein, the reaction is carried out at elevated pressure.

Unless otherwise indicated, the term "alkyl" as referred to herein, as well as the alkyl moieties of other groups referred to herein (e.g., alkoxy), may be linear or branched (such as methyl, ethyl, n-propyl, isopropyl, n-butyl, iso-butyl, secondary-butyl, tertiary-butyl), and they may also be cyclic (e.g., cyclopropyl, or cyclobutyl); optionally substituted by 1 to 3 suitable substituents as defined below such as fluoro, chloro, trifluoromethyl, $(C_1-C_6)$alkoxy, $(C_6-C_{10})$aryloxy, trifluoromethoxy, difluoromethoxy or $(C_1-C_6)$alkyl. The phrase "each of said alkyl" as used herein refers to any of the preceding alkyl moieties within a group such alkoxy, alkenyl or alkylamino.

Unless otherwise indicated, the terms "halo" and "halogen" are used herein to mean fluoro, chloro, bromo or iodo, or fluorine, chlorine, bromine or iodine, respectively, while the term "halide" is used herein to refer to the fluoride, chloride, bromide or iodide anions.

As used herein, the term "halo-substituted alkyl" refers to an alkyl radical as described above substituted with one or more halo including, but not limited to, chloromethyl, dichloromethyl, trichloromethyl, fluoromethyl, difluoromethyl, trifluoromethyl, 2,2,2-trichloroethyl, and the like; optionally substituted by 1 to 3 suitable substituents as defined below such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

As used herein, the term "alkenyl" means straight or branched chain unsaturated radicals of 2 to 6 carbon atoms, including, but not limited to ethenyl, 1-propenyl, 2-propenyl (allyl), iso-propenyl, 2-methyl-1-propenyl, 1-butenyl, 2-butenyl, and the like; optionally substituted by 1 to 3 suitable substituents as defined below such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

As used herein, the term "alkynyl" is used herein to mean straight or branched hydrocarbon chain radicals of 2 to 6 carbon atoms having one triple bond including, but not limited to, ethynyl, propynyl, butynyl, and the like; optionally substituted by 1 to 3 suitable substituents as defined below such as fluoro, chloro, trifluoromethyl, $(C_1-C_6)$ alkoxy, $(C_6-C_{10})$aryloxy, trifluoromethoxy, difluoromethoxy or $(C_1-C_6)$alkyl.

As used herein, the term "alkoxy" refers to O-alkyl groups, wherein alkyl is as defined above.

As used herein, the term "alkoxycarbonyl" refers to an alkoxy radical as described above connected to a carbonyl group (>C=O), which, in turn, serves as the point of attachment.

The phrase "pharmaceutically acceptable salt(s)", as used herein, unless otherwise indicated, includes salts of acidic or basic groups which may be present in the compounds of the present invention. The compounds prepared by the processes of the present invention that are basic in nature are capable of forming a wide variety of salts with various inorganic and organic acids. The acids that may be used to prepare pharmaceutically acceptable acid addition salts of such basic compounds of the present invention are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds prepared by the processes of the present invention that include an amino moiety may form pharmaceutically acceptable salts with various amino acids, in addition to the acids mentioned above.

The present invention includes processes for preparing a compound of formula 1 wherein one or more hydrogen, carbon, nitrogen or other atoms are replaced by isotopes thereof. Such compounds are useful as diagnostic tools and in metabolic, pharmacokinetic and binding studies. Examples of isotopes that can be utilized in this invention include isotopes of hydrogen, carbon, nitrogen, oxygen, sulfur, fluorine and chlorine, such as $^2H$, $^3H$, $^{13}C$, $^{14}C$, $^{15}N$, $^{18}O$, $^{17}O$, $^{35}S$, $^{18}F$, and $^{36}Cl$, respectively. Processes of the present invention which utilize the aforementioned isotopes and/or other isotopes of other atoms are within the scope of this invention. Certain isotopically-labelled compounds prepared by the processes of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds prepared by the processes of this invention can generally be prepared by carrying out the procedures disclosed in the Schemes and/or in the Examples below, by substituting a readily available isotopically labelled reagent for a non-isotopically labelled reagent.

DETAILED DESCRIPTION OF THE INVENTION

The process of the present invention may be carried out according to Scheme 1 below and the description that follows. Substituents $R^1$–$R^4$ in Schemes 1 and 2 are as defined above for the compound of formula 1.

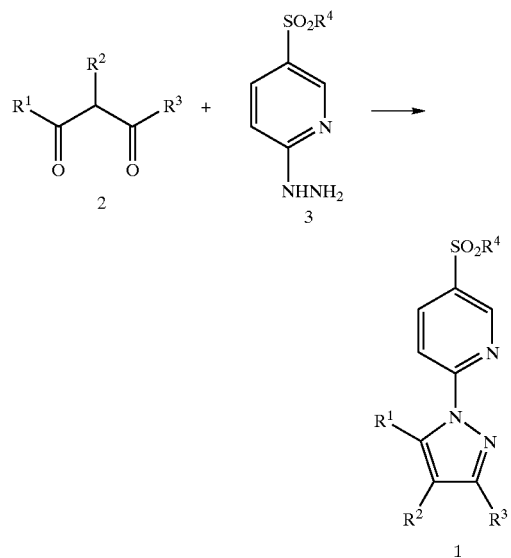

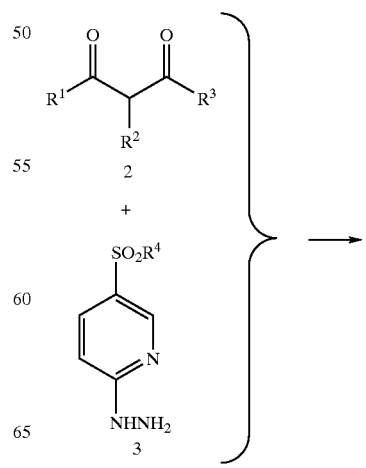

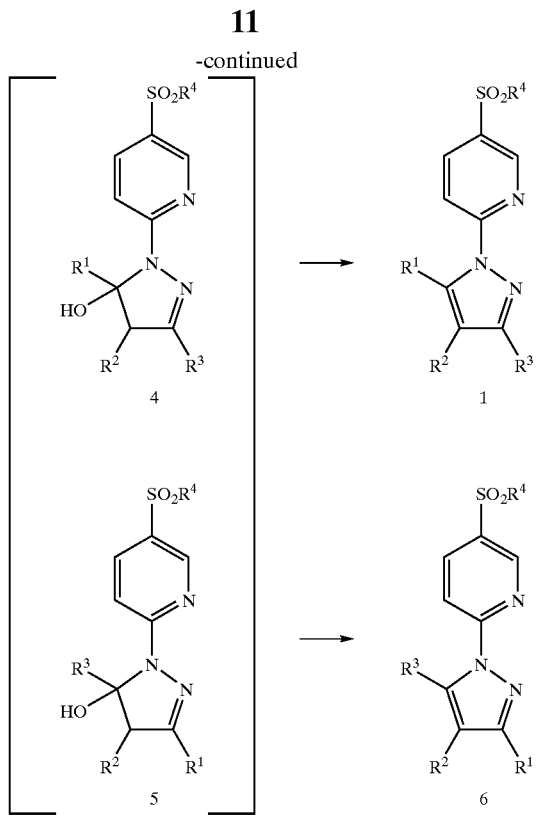

Schemes 1 and 2 given above are illustrative only and are described in further detail below and in the Examples further hereinbelow.

Co-pending U.S. application Ser. No. 09/724,446, filed Nov. 28, 2000, which is herein incorporated by reference in its entirety, discloses processes for preparing pyrazole compounds which generically encompass compounds of formula 1, as well as specific examples of the preparation of certain compounds of the formula 1, which as shown in Scheme 1, comprise heating to reflux a mixture of a compound of formula 2, a compound of formula 3 and an organic solvent under acidic neutral or basic conditions, preferably in the present of an acid or the acid salt of a compound of formula 3. Numerous solvents are described as suitable for the reaction, including alcohols, which are preferred, e.g., ethanol and isopropanol, as well as dimethyl sulfoxide (DMSO), N,N-dimethylformamide (DMF), N,N-dimethylacetamide (DMA), N-methyl-2-pyrrolidinone (NMP), benzene, toluene and chloroform. The preferred acids in application Ser. No. 09/724,446 include hydrochloric, acetic, trifluoroacetic, p-toluenesulfonic and sulfuric acid. The temperature for the reaction in application Ser. No. 09/724,446 is from about 0° C. to about 140° C., preferably at about the reflux temperature of the polar solvent. The Examples in application Ser. No. 09/724,446 describe the preparation of specific pyrazole compounds according to the method shown in Scheme 1 above, where the solvent is ethyl acetate or trifluoroethanol, wherein a compound of formula 2 and a compound of formula 3 are heated to reflux in trifluoroethanol containing sulfuric acid, or in ethyl acetate.

Compounds of formula 2 may be prepared according to Ser. No. 09/724,446, Preparation 5 and Preparation 6, as well as the methods described in *Aust. J. Chem.*, 1977, 30, 229 and *Heterocycles*, 1990, 31, 1951, as well as by methods which are known in the art. Compounds of formula 3 may be prepared according to Ser. No. 09/724,446, Preparation 2 and Alternate Preparation 2, and as described further hereinbelow, as well as by methods which are known in the art. It is to be noted that PCT publication WO 01/40216, published on Jun. 7, 2001, corresponds to Ser. No. 09/724,446. Compounds of formula 2 are also taught in U.S. application Ser. No. 09/723,609; the European application 310533.5 corresponding thereto was published on Jun. 6, 2001, as EP 1104758.

It has been discovered that the pyrazole compounds of formula 1 are particularly preferred among the compounds disclosed in application Ser. No. 09/724,446. However, applicants have discovered, as shown in Scheme 2, that using the processes disclosed in application Ser. No. 09/724,446 to prepare a compound of formula 1 results in the formation of a mixture of a compound of formula 1 and its regioisomer (i.e., a compound having the formula 6, where the positions of $R^1$ and $R^3$ are reversed compared to the compound formula 1). Accordingly, it is an object of this invention to provide a process for the regioselective production of the compound of formula 1 with high yield and purity.

The regioselective production of the compounds of formula 1 (i.e., while avoiding the simultaneous production of 6) with a yield and purity suitable for commercial use has presented several difficulties. Applicants have found that while it is possible to recrystallize 1 from the mixtures of 1 and 6 resulting from the process shown in Scheme 1, the overall yield of 1 is poor, and the amount of 1 that can be successfully separated by recrystallization decreases as the amount of 6 in the mixture increases. Applicants' further investigations have revealed that reacting the compounds of formulas 2 and 3 at low temperatures, e.g., preferably less than about 40° C. (in suitable solvents, such as alcohols), favors the regioselective production of the compound of formula 1. However, because the compound of formula 1 is poorly soluble at low temperatures, the compounds of formula 1 and formula 4 co-precipitate, preventing the progression of the compound of formula 4 to the final product 1 and resulting in poor yields and the presence of the compound of formula 4 as a major impurity. On the other hand, maintaining the reaction temperature high enough to keep both compounds (1 and 4) in solution, allowing the reaction to proceed to completion, causes another problem, namely, the production of the compound of formula 5 and the progression of 5 to the compound of formula 6 as a major impurity.

Applicants solved these problems by discovering unexpectedly that the use of water as a co-solvent in the reaction provided the following benefits: (1) the production of the compounds of formula 5 and formula 6 are minimized, thereby resulting in the formation of the compound of formula 1 with high regioselectivity; and (2) the compound of formula 1 is formed with high yield. Applicants have further discovered that these advantages result regardless of whether water is combined with the other ingredients from the start of the reaction, or whether the water is added after the formation of substantial amounts of the compound of formula 4. In addition, the use of water allows the regioselective production of the compound of formula 1 over a broad range of temperatures.

The compounds prepared by the processes of the present invention that are basic in nature are capable of forming a wide variety of different salts with various inorganic and organic acids. Although such salts must be pharmaceutically acceptable for administration to mammals, it is often desirable in practice to initially isolate a compound prepared by the processes of the present invention from the reaction mixture as a pharmaceutically unacceptable salt and then simply convert the latter back to the free base compound by treatment with an alkaline reagent, for use in subsequently reactions or for the preparation of a pharmaceutically acceptable acid addition salt. The acid addition salts of the base compounds prepared by the processes of this invention are readily prepared by treating the base compound with a substantially equivalent amount of the chosen mineral or organic acid in an aqueous solvent medium or in a suitable organic solvent. Upon careful evaporation of the solvent, the desired solid salt is readily obtained. The desired salt can also be precipitated from a solution of the free base in an organic solvent by adding to the solution an appropriate mineral or organic acid.

The compounds of formula 1 prepared by the processes of this invention and the pharmaceutically acceptable salts thereof (hereinafter "the active compounds"), may be administered through oral, parenteral, topical, or rectal routes in the treatment or alleviation of inflammation and other inflammation associated disorders, such as arthritis, neurodegeneration and colon cancer, in mammals, preferably humans, dogs, cats or livestock.

In general, the active compounds are most desirably administered in dosages ranging from about 0.2 mg per kg body weight per day (mg/kg/day) to about 200 mg/kg/day in single or divided doses (i.e., from 1 to 4 doses per day), although variations will necessarily occur depending upon the species, weight and condition of the subject being treated and the particular route of administration chosen. However, a dosage level that is in the range of about 4 mg/kg/day to about 50 mg/kg/day is most desirably employed. Variations may nevertheless occur depending upon the species of mammal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds may be administered alone or in combination with pharmaceutically acceptable carriers or diluents by the routes previously indicated, and such administration may be carried out in single or multiple doses. More particularly, the active compounds may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the active compounds are present in such dosage forms at concentration levels ranging from about 5.0% to about 70% by weight. Numerous examples of acceptable carriers, diluents, excipients, disintegrants, lubricating agents, sweetening and flavoring agents, coloring matter or dyes, emulsifying agents, suspending agents, diluents, buffers, creams, jellies, gels, pastes, patches, ointments, etc. useful in the preparation of pharmaceutical compositions and formulations are known in the art, see, *Remington's Pharmaceutical Sciences*, Mack Publishing Company, Easton, Pa., 18th Edition, Gennaro, ed. (1990), pages 1545–1580. The preparation of all these compositions under sterile conditions is readily accomplished by standard pharmaceutical techniques will known to those skilled in the art.

For administration to animals other than humans, such as cattle or domestic animals, such as dogs or cats, particularly dogs, the active compounds may be administered in the feed of the animals or orally as a drench composition.

The active compounds may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The active compounds may also be coupled with soluble polymers as targetable drug carriers. Such polymers can include polyvinylpyrrolidone, pyran copolymer, polyhydroxypropylmethacrylamide phenyl, polyhydroxyethylaspartamide-phenol, or polyethyleneoxide-polylysine substituted with palmitoyl residues. Furthermore, the active compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

One of ordinary skill in the art will appreciate that the compounds of formula 1 prepared by the processes of the invention are useful in treating a diverse array of diseases. One of ordinary skill in the art will also appreciate that when using the compounds of formula 1 prepared by the processes of the invention in the treatment of a specific disease that the compounds may be combined with various existing therapeutic agents used for that disease.

For the treatment of rheumatoid arthritis, the compounds of formula 1 prepared by the processes of the invention may be combined with agents such as TNF-$\alpha$ inhibitors such as anti-TNF monoclonal antibodies and TNF receptor immunoglobulin molecules (such as Enbrel®), low dose methotrexate, lefunimide, hydroxychloroquine, d-penicilamine, auranofin or parenteral or oral gold.

The compounds of formula 1 prepared by the processes of the invention can also be used in combination with existing therapeutic agents for the treatment of osteoarthritis. Suitable agents to be used in combination include standard non-steroidal anti-inflammatory agents (hereinafter NSAID's) such as etodolac, piroxicam, diclofenac, propionic acids such as naproxen, flurbiprofen, fenoprofen, carprofen, ketoprofen and ibuprofen, fenamates such as meclofenamic acid, mefenamic acid, indomethacin, sulindac, apazone, pyrazolones such as phenylbutazone, salicylates such as aspirin, COX-2 inhibitors such as celecoxib and rofecoxib, analgesics and intraarticular therapies such as corticosteroids and hyaluronic acids such as hyalgan and synvisc.

The compounds of formula 1 prepared by the processes of the present invention may be administered in combination with inhibitors of other mediators of inflammation, comprising one or more members selected from the group consisting essentially of the classes of such inhibitors and examples thereof which include, matrix metalloproteinase inhibitors, aggrecanase inhibitors, TACE inhibitors, leucotriene receptor antagonists, IL-1 processing and release inhibitors, ILra, $H_1$-receptor antagonists; kinin-$B_1$- and $B_2$-receptor antagonists; prostaglandin inhibitors such as PGD-, PGF- PGI$_2$-, and PGE-receptor antagonists; thromboxane A$_2$ (TXA2-) inhibitors; 5- and 12-lipoxygenase inhibitors; leukotriene LTC$_4$-, LTD$_4$/LTE$_4$-, and LTB$_4$-inhibitors; PAF-receptor antagonists; gold in the form of an aurothio group together with various hydrophilic groups; immunosuppressive agents, e.g., cyclosporine, azathioprine, and methotrexate; anti-inflammatory glucocorticoids; penicillamine; hydroxychloroquine; anti-gout agents, e.g., colchicine, xanthine oxidase inhibitors, e.g., allopurinol, and uricosuric agents, e.g., probenecid, sulfinpyrazone, and benzbromarone.

The compounds of formula 1 prepared by the processes of the present invention may also be used in combination with anticancer agents such as endostatin and angiostatin or cytotoxic drugs such as adriamycin, daunomycin, cis-platinum, etoposide, taxol, taxotere and alkaloids, such as vincristine, and antimetabolites such as methotrexate.

The compounds of formula 1 prepared by the processes of the present invention may also be used in combination with anti-hypertensives and other cardiovascular drugs intended to offset the consequences of atherosclerosis, including hypertension, myocardial ischemia including angina, congestive heart failure, and myocardial infarction, selected from vasodilators such as hydralazine, β-adrenergic receptor antagonists such as propranolol, calcium channel blockers such as nifedipine, α$_2$-adrenergic agonists such as clonidine, α-adrenergic receptor antagonists such as prazosin, and HMG-CoA-reductase inhibitors (anti-hypercholesterolemics) such as lovastatin or atorvastatin.

The compound of formula 1 prepared by the processes of the present invention may also be administered in combination with one or more antibiotic, antifungal, antiprotozoal, antiviral or similar therapeutic agents.

The compounds of formula 1 prepared by the processes of the present invention may also be used in combination with CNS agents such as antidepressants (such as sertraline), anti-Parkinsonian drugs (such as L-dopa, requip, mirapex, MAOB inhibitors such as selegine and rasagiline, comP inhibitors such as Tasmar, A-2 inhibitors, dopamine reuptake inhibitors, NMDA antagonists, nicotine agonists, dopamine agonists and inhibitors of neuronal nitric oxide synthase), and anti-Alzheimer's drugs such as donepezil, tacrine, COX-2 inhibitors, propentofylline or metryfonate.

The compounds of formula 1 prepared by the processes of the present invention may also be used in combination with osteoporosis agents such as roloxifene, lasofoxifene, droloxifene or fosomax and immunosuppressant agents such as FK-506 and rapamycin.

The present invention also further comprises formulating the compound of formula 1 prepared by the processes of the present invention alone or with one or more other therapeutic agents which are to form the intended combination, including wherein said different drugs have varying half-lives, by creating controlled-release forms of said drugs with different release times which achieves relatively uniform dosing; or, in the case of non-human patients, a medicated feed dosage form in which said drugs used in the combination are present together in admixture in said feed composition. There is further provided in accordance with the present invention co-administration in which the combination of drugs is achieved by the simultaneous administration of said drugs to be given in combination; including co-administration by means of different dosage forms and routes of administration; the use of combinations in accordance with different but regular and continuous dosing schedules whereby desired plasma levels of said drugs involved are maintained in the patient being treated, even though the individual drugs making up said combination are not being administered to said patient simultaneously.

The following Examples further illustrate the method and intermediates of the present invention. It is to be understood that the present invention is not limited to the specific details of the Examples provided below.

Analytical Methods

The amounts of starting materials, intermediates and products were determined by HPLC unless otherwise specified. The column used was a Zorbx RX-C8 CN column of 4.5 mm interior diameter, 150 mm in length, in a Hewlett Packard 1100 system at 2 mL/minute, measuring absorbance at 210 nm. Gradient elution was used with following the program: 15-minute hold at 60% A/40% B, 10-minute ramp to 90% A/10% B, 5-minute ramp to 60% A/40% B. Solvent A: solution of 0.2% phosphoric acid in HPLC water; Solvent B: 85% Acetonitrile in HPLC water.

EXAMPLE 1

5-methylsulfonyl-2-[5-phenyl-3-difluoromethyl-1H-pyrazol-1-yl]pyridine

To 12.2 kg of 5-(methylsulfonyl)-2-hydrazinyl-pyridine (64.1 moles) was charged isopropanol (45 gallons) followed by 4,4-difluoro-1-phenyl-1,3-butanedione (12.0 kg, 61.5 moles, 0.96 eq.) as a melt, followed by 45 gallons of isopropanol. The slurry was stirred for 15 minutes, then 3.6 L of concentrated sulfuric acid was added (slight exotherm) (30V of isopropanol total). The reaction was heated to 75° C. and held for 1 hour. The pot was then cooled to 20–30° C. After reaction completion assay, 126 gallons (40V) of water was added (slight exotherm, reaction temp kept below 45° C.) and the reaction product was granulated for 2 hours. The product was filtered on a 36-inch nutche filter dressed with a poly cloth in less than 2 hours. The filter cake was rinsed with an additional 12 gallons (4V) of water, and the cake was blown dry for 12 hours. The product contained 2.2% of compound 6 as the major impurity (by HPLC; retention time 5.1 minutes). Analytical data: HPLC retention time (title compound) 8.4 minutes; MS: 349.36 (calc), M+1=350.1; $^1$H NMR in CDCl$_3$: 8.75 doublet, (1H), 8.26 Quartet (1H), 7.38 multiplet (3H), 7.36 doublet (2H), 6.70 multiplet (2H), 3.08, Singlet, (3H); $^{13}$C NMR in CDCl$_3$: 15.3, 149.3, 147.9, 146.6, 138.1, 130.27, 133.5, 130.0, 129.1, 128.7, 117.9, 113.4, 111.1, 108.1, 107.7, 45.).

EXAMPLE 2

5-methylsulfonyl-2-[5-phenyl-3-difluoromethyl-1H-pyrazol-1-yl]pyridine

To 120 g of 5-(methylsulfonyl)-2-hydrazinyl-pyridine [CP-675,775] (0.641 moles) was charged isopropanol (900 mL) followed by 4,4-difluoro-1-phenyl-1,3-butanedione (122 g, 0.615 moles, 0.96 eq.) as a melt, followed by 900 mL of isopropanol. The slurry was stirred for 15 minutes, then 36 mL of concentrated sulfuric acid was added (slight exotherm) (15 volumes of isopropanol total). The reaction was stirred for 6 hours at 20–30° C., 2.4 L (20 volumes) of water was added (slight exotherm, reaction temperature kept below 45° C.) and the reaction was granulated for 2 days. The product was filtered and was rinsed with water. The product contained less than 0.5% of compound 6 (retention time 5.1 minutes). Analytical data: HPLC retention time (title compound) 8.4 minutes; MS: 349.36 (calc), M+1=

350.1; $^1$H NMR in CDCl$_3$: 8.75 doublet, (1H), 8.26 Quartet (1H), 7.38 multiplet (3H), 7.36 doublet (2H), 6.70 multiplet (2H), 3.08, Singlet, (3H); $^{13}$C NMR in CDCl$_3$: 15.3, 149.3, 147.9, 146.6, 138.1, 130.27, 133.5, 130.0, 129.1, 128.7, 117.9, 113.4, 111.1, 108.1, 107.7, 45.

EXAMPLE 3

5-methylsulfonyl-2-[5-phenyl-3-difluoromethyl-1H-pyrazol-1-yl]pyridine

To a clean and dry nitrogen purged 1 L round-bottom flask under nitrogen atmosphere was charged 25.6 g of 5-(methylsulfonyl)-2-hydrazinyl-pyridine (0.14 moles), 512 mL water (20 volumes) and 16 mL of concentrated H$_2$SO$_4$ (0.063 volumes). In a separate 500 mL 1-neck round-bottom flask, was prepared a solution of 384 mL of isopropanol (15 volumes) and 26.01 g (0.13 moles) of 4,4-difluoro-1-phenyl-1,3-butanedione. The isopropanol/4,4-difluoro-1-phenyl-1,3-butanedione solution was added to the 5-(methylsulfonyl)-2-hydrazinyl-pyridine reaction mixture keeping the pot temperature less than 25° C. After addition, the mixture was stirred at 22° C. for 2.0 hours and sampled for disappearance of starting material. When the starting materials had disappeared (less than 15 remaining), the pot was then heated to 40° C. for 5.5 hours until disappearance of the intermediate. The resulting slurry was filtered and washed with water to achieve a pH 6–7 of the filtrate. The solids were then charged to a 250 mL 3-neck round-bottom flask. To the flask was added: 31.25 mL water (1.2 volumes) and 31.25 mL isopropanol (1.2 volumes). The mixture was heated to reflux (85° C.) for 30 minutes. The pot was allowed to cool to 28° C. and the solids were isolated by filtration and washed with 20 mL isopropanol. The solids were dried in a vacuum oven at 45° C. The product was obtained with 87% yield and contained 0.54% of the compound of formula 6 (retention time 5.1 minutes). Analytical data: HPLC retention time (title compound) 8.4 minutes; MS: 349.36 (calc), M+1=350.1; $^1$H NMR in CDCl$_3$: 8.75 doublet, (1H), 8.26 Quartet (1H), 7.38 multiplet (3H), 7.36 doublet (2H), 6.70 multiplet (2H), 3.08, Singlet, (3H); $^{13}$C NMR in CDCl$_3$: 15.3, 149.3, 147.9, 146.6, 138.1, 130.27, 133.5, 130.0, 129.1, 128.7, 117.9, 113.4, 111.1, 108.1, 107.7, 45.

EXAMPLE 4

5-methylsulfonyl-2-[5-phenyl-3-difluoromethyl-1H-pyrazol-1-yl]pyridine

To a clean and dry nitrogen purged 22 L round bottom flask under nitrogen atmosphere was charged: 500 g of 5-(methylsulfonyl)-2-hydrazinyl-pyridine (2.67 moles), 10 L water (20 volumes) and 579 mL of concentrated H$_2$SO$_4$ (0.063 volumes). In a separate 12 L 3-neck round-bottomed flask was prepared a solution of 7500 mL of isopropanol (15 volumes) and 508 g (2.56 moles) of 4,4-difluoro-1-phenyl-1,3-butanedione. The isopropanol/4,4-difluoro-1-phenyl-1,3-butanedione solution was added to the mixture containing the 5-(methylsulfonyl)-2-hydrazinyl-pyridine, keeping the pot temperature below 30° C. After addition of the 4,4-difluoro-1-phenyl-1,3-butanedione solution, the mixture was stirred at 24° C. for 1.0 hour and sampled for disappearance of 5-(methylsulfonyl)-2-hydrazinyl-pyridine by HPLC. The pot was then heated to 40° C. for 2 hours until disappearance of the intermediate compound of formula 4 and the resulting slurry was filtered and washed with water to achieve a pH of the filtrate of from about 6–7. The solids were then charged to a 5L 3-neck round-bottom flask. To the flask was added 1250 mL water (2.5 volumes) and 1250 mL isopropanol (2.5 volumes). The mixture was heated to reflux (85° C.) for 2 hours. The pot was then cooled to 40° C. and then stirred overnight. The solids were isolated by filtration, washed with 2 L isopropanol, and dried in a vacuum oven at 45° C. The compound of formula 6 was present at a level of 1.2% by HPLC (retention time 5.1 minutes). Analytical data: HPLC retention time (title compound) 8.4 minutes; MS: 349.36 (calc), M+1=350.1; $^1$H NMR in CDCl$_3$: 8.75 doublet, (1H), 8.26 Quartet (1H), 7.38 multiplet (3H), 7.36 doublet (2H), 6.70 multiplet (2H), 3.08, Singlet, (3H); $^{13}$C NMR in CDCl$_3$: 15.3, 149.3, 147.9, 146.6, 138.1, 130.27, 133.5, 130.0, 129.1, 128.7, 117.9, 113.4, 111.1, 108.1, 107.7, 45.

PREPARATION 1

In addition to the methods disclosed in Ser. Nos. 09/724,446 and 09/723,609 for preparing compounds of formula 2, applicants have utilized the following process for preparing 1-(phenyl)-1,3-butanediones, which comprises treating a compound of the formula

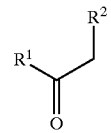

with an optionally substituted ester of the formula

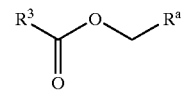

wherein $R^a$ is $(C_1-C_3)$alkyl, in a suitable anhydrous organic solvent, such as ethylene glycol dimethyl ether, in the presence of a base, preferably sodium methoxide. Preferably, $R^a$ is ethyl. The product compound of formula 2 is preferably purified by recrystallization from an alcohol/water mixture, preferably methanol/water.

PREPARATION 2

In addition to the methods disclosed in Ser. No. 09/724,446 for preparing compounds of formula 3, applicants have utilized the following process for preparing 5-(alkane sulfonyl)-2-hydrazinyl-pyridines, comprising the steps of: (a) treating 2,5-dibromopyridine with a Grignard reagent, such as propyl magnesium halide or isopropylmagnesium halide, in suitable solvent, such as diethyl ether, tetrahydrofuran, glyme or diglyme, at a temperature from about −20° C. to about 10° C., for a period of from about 0.5 hours to about 4 hours, preferably about 45 minutes, followed by (b) sulfonylation with an agent such as alkanesulfonyl fluoride, alkanesulfonyl chloride or alkanesulfonic anhydride, to afford 2-bromo-5-(alkane sulfonyl)-pyridine, followed by (c) reaction of the product of (b) with hydrazine hydrate in a presence of an amine, in a suitable solvent, at a temperature of from about 20° C. to about 100° C., preferably about 70° C., for a period of from about 3 hours to about 24 hours, preferably about 5 hours, to yield 2-hydrazinyl-5-(alkane sulfonyl)-pyridine.

Preferably, the Grignard reagent is isopropylmagnesium chloride, and the solvent is tetrahydrofuran. Preferably, the sulfonylating agent is methanesulfonyl chloride. For the hydrazinolysis, preferably the amine is triethylamine, diisopropylethylamine, 2,6-lutidine, N,N,N',N'- tetramethylethylenediamine, more preferably triethylamine, and the solvent is water, dichloromethane, dichloroethane, toluene, preferably water.

As a specific, but non-limiting example, applicants have prepared 5-(methanesulfonyl)-2-hydrazinyl-pyridine according to this process, as follows:

(a) 2-Bromo-5-(methanesulfonyl)-pyridine (i) To a solution of 2,5-dibromopyridine (50 g, 211 mmol) in tetrahydrofuran (175 mL) at 0° C. was added 2.0 M isopropylmagnesium chloride (274 mmol) at a rate which maintained the temperature below 8° C. The reaction mixture was stirred at 0° C. for 45 minutes, then cooled to −15° C. A solution of methanesulfonyl chloride (32.2 g, 281 mmol) in tetrahydrofuran (40 mL) was added to the reaction mixture at a rate which maintained the temperature below 5° C. The reaction mixture was allowed to warm to room temperature and then quenched with water (500 mL) and tert-butylethylether (300 mL). The layers were separated, the aqueous layer was extracted twice with tert-butylethylether (2×200 mL). The combined organic extracts were washed with water (200 mL) and concentrated. The crude product was crystallized from toluene (110 mL) and the solids were filtered to afford 29.4 g (59% yield) of 2-bromo-5-(methanesulfonyl)-pyridine. Analytical data: $^1$H NMR (300 MHz, CDCl$_3$) δ 3.13 (s, 3H), 7.73 (d, J=8.3 Hz, 1H), 8.07 (dd, J$_1$=8.3 Hz, J$_2$=2.7 Hz, 1H), 8.91 (d, J=2.5 Hz, 1H).

(ii) In the reaction described above in (i), the use of methanesulfonyl fluoride as the sulfonylating agent provided the product with 53% yield.

(iii) In the reaction described above in (i), the use of methanesulfonyl anhydride as the sulfonylating agent provided the product with 50% yield.

(b) 2-Hydrazinyl-5-(methanesulfonyl)-pyridine

A suspension of 2-bromo-5-(methanesulfonyl)-pyridine (7.3 g, 116 mmol), triethylamine (14.7 g, 145 mmol), and hydrazine hydrate (7.26 g, 145 mmol) in water (205 mL) was heated to 70° C. The reaction mixture became homogenous before the product started to precipitate out of this mixture (after 90 minutes). The reaction mixture was stirred at 70° C. for total of 5 hours and then was allowed to cool to room temperature and stirred for 18 hours. The precipitated product was collected by filtration, dried and recrystallized from hot ethanol to afford 2-hydrazinyl-5-(methanesulfonyl)-pyridine in 86% yield. Analytical data: $^1$H NMR (300 MHz, CDCl$_3$) δ 3.12 (s, 3H), 4.44 (br s, 2H), 6.80 (br d, J=8.7 Hz, 1H), 7.81 (dd, J$_1$=9.0 Hz, J$_2$=2.4 Hz, 1H), 8.38 (d, 2.3 Hz, 1H), 8.57 (br s, 1H).

What is claimed is:

1. A compound of the formula 4:

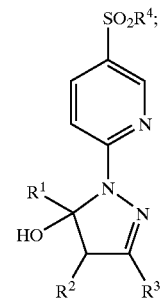

4 wherein

R$^1$ is phenyl optionally substituted by 1–3 substituents independently selected from the group consisting of halo, hydroxy, cyano, mercapto, (C$_1$–C$_6$)alkyl, (C$_2$–C$_6$) alkenyl, (C$_1$–C$_6$)alkoxy, —OCF$_3$, (C$_1$–C$_6$)alkyl-S—, (C$_1$–C$_6$)alkyl-S(=O)—, (C$_1$–C$_6$)alkyl-SO$_2$—, amino, (C$_1$–C$_6$)alkylamino, di[(C$_1$–C$_6$)alkyl]amino, H$_2$N—(C=O)—, (C$_1$–C$_6$)alkyl-NH—(C=O)— and formyl;

R$^2$ is hydrogen, halo or (C$_1$–C$_6$)alkyl;

R$^3$ is (C$_1$–C$_6$)alkyl optionally substituted with one to three halo atoms; and R$^4$ is (C$_1$–C$_6$)alkyl.

* * * * *